US010109862B2

(12) United States Patent
Ahn et al.

(10) Patent No.: US 10,109,862 B2
(45) Date of Patent: Oct. 23, 2018

(54) ANODE FOR SECONDARY BATTERY AND SECONDARY BATTERY COMPRISING THE SAME

(71) Applicant: LG Chem, Ltd., Seoul (KR)

(72) Inventors: Kyoung-Ho Ahn, Daejeon (KR); Chul-Haeng Lee, Daejeon (KR); Doo-Kyung Yang, Daejeon (KR); Min-Jung Kim, Daejeon (KR); Jung-Hoon Lee, Daejeon (KR); Yi-Jin Jung, Daejeon (KR)

(73) Assignee: LG Chem, Ltd. (KR)

( * ) Notice: Subject to any disclaimer, the term of this patent is extended or adjusted under 35 U.S.C. 154(b) by 326 days.

(21) Appl. No.: 14/549,820

(22) Filed: Nov. 21, 2014

(65) Prior Publication Data
US 2015/0079467 A1 Mar. 19, 2015

Related U.S. Application Data

(63) Continuation of application No. PCT/KR2013/006122, filed on Jul. 10, 2013.

(30) Foreign Application Priority Data

Jul. 10, 2012 (KR) .......................... 10-2012-0075122

(51) Int. Cl.
H01M 4/00 (2006.01)
H01M 4/62 (2006.01)
(Continued)

(52) U.S. Cl.
CPC .............. *H01M 4/62* (2013.01); *C07F 9/091* (2013.01); *C08F 222/1006* (2013.01);
(Continued)

(58) Field of Classification Search
CPC .... H01M 4/131; H01M 4/485; H01M 4/0404; H01M 4/62; H01M 4/366; H01M 4/1391
See application file for complete search history.

(56) References Cited

U.S. PATENT DOCUMENTS

2005/0266150 A1* 12/2005 Yong ..................... H01M 2/166
427/58
2010/0003604 A1 1/2010 Kang et al.
(Continued)

FOREIGN PATENT DOCUMENTS

CN 102403509 A 4/2012
JP 2001176498 A 6/2001
(Continued)

OTHER PUBLICATIONS

International Search Report from PCT/KR2013/006122, dated Oct. 11, 2013.

*Primary Examiner* — Nicholas P D'Aniello
(74) *Attorney, Agent, or Firm* — Lerner, David, Littenberg, Krumholz & Mentlik, LLP

(57) ABSTRACT

Disclosed are an anode for secondary batteries and a secondary battery including the same. The anode includes an anode mixture including an anode active material, coated on a current collector, wherein the anode active material includes lithium titanium oxide (LTO) particles provided on surfaces thereof with a cross-linked polymer coating layer, wherein the LTO particles with the cross-linked polymer coating layer formed thereon retain a porous structure formed therebetween, and a cross-linked polymer of the coating layer is a phosphate-based compound.

18 Claims, 1 Drawing Sheet

(51) Int. Cl.
  *H01M 4/131* (2010.01)
  *H01M 4/1391* (2010.01)
  *H01M 4/485* (2010.01)
  *H01M 4/04* (2006.01)
  *C07F 9/09* (2006.01)
  *C08F 222/10* (2006.01)
  *C08F 230/02* (2006.01)
  *H01M 4/36* (2006.01)
  *H01M 10/052* (2010.01)
  *C09D 133/14* (2006.01)
  *C09D 143/02* (2006.01)

(52) U.S. Cl.
  CPC .......... *C08F 230/02* (2013.01); *C09D 133/14* (2013.01); *C09D 143/02* (2013.01); *H01M 4/0404* (2013.01); *H01M 4/131* (2013.01); *H01M 4/1391* (2013.01); *H01M 4/366* (2013.01); *H01M 4/485* (2013.01); *H01M 10/052* (2013.01); *H01M 2220/10* (2013.01); *H01M 2220/20* (2013.01); *Y02E 60/122* (2013.01); *Y02P 70/54* (2015.11); *Y02T 10/7011* (2013.01)

(56) References Cited

U.S. PATENT DOCUMENTS

| | | |
|---|---|---|
| 2012/0058395 A1 | 3/2012 | Harada et al. |
| 2012/0171570 A1 | 7/2012 | Huang et al. |
| 2013/0252077 A1* | 9/2013 | Iwasaki .................. H01M 4/13 429/163 |

FOREIGN PATENT DOCUMENTS

| | | |
|---|---|---|
| JP | 2010061930 A | 3/2010 |
| JP | 2012-059467 A | 3/2012 |
| JP | 2012119092 A | 6/2012 |
| KR | 10-0744835 B1 | 7/2007 |
| KR | 2011-0010516 A | 2/2011 |
| KR | 20140008263 A | 1/2014 |
| WO | 2008013417 A1 | 1/2008 |

\* cited by examiner

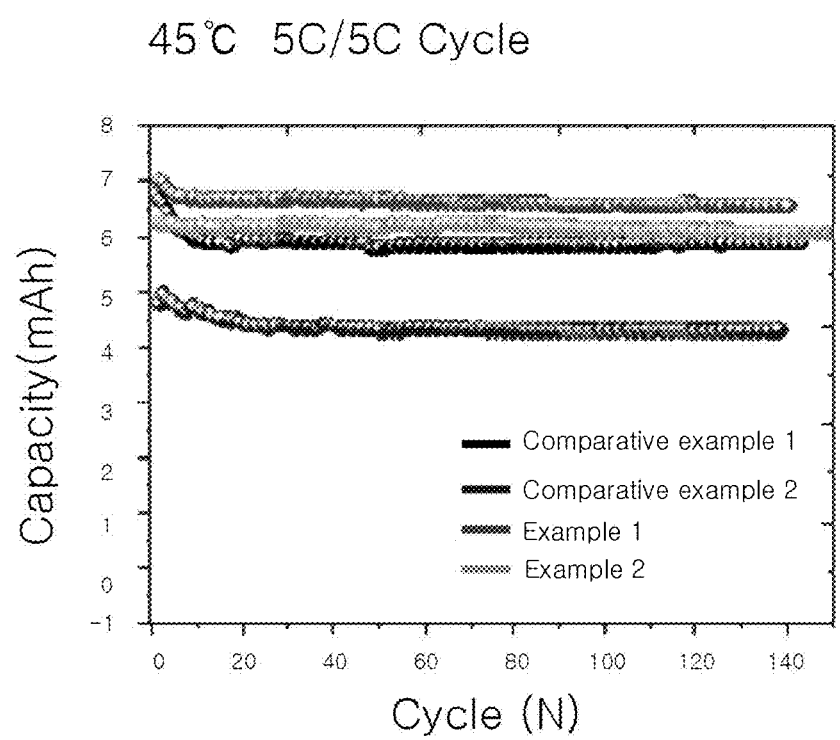

ANODE FOR SECONDARY BATTERY AND SECONDARY BATTERY COMPRISING THE SAME

CROSS REFERENCE TO RELATED APPLICATIONS

The present application is a continuation of International Application No. PCT/KR2013/006122 filed Jul. 10, 2013, which claims the benefit of the filing date of Korean Patent Application No. 10-2012-0075122 filed Jul. 10, 2012, the disclosures of which are hereby incorporated herein by reference.

TECHNICAL FIELD

The present invention relates to an anode for secondary batteries in which an anode mixture including an anode active material is coated on a current collector, wherein the anode active material includes lithium titanium oxide (LTO) particles provided on a surface thereof with a cross-linked polymer coating layer, wherein the LTO particles with the cross-linked polymer coating layer formed thereon have a porous structure formed therebetween, and a cross-linked polymer of the coating layer is a phosphate-based compound and a secondary battery including the same.

BACKGROUND ART

As mobile device technology continues to develop and demand therefor continues to increase, demand for secondary batteries as energy sources is rapidly increasing. Among these secondary batteries, lithium secondary batteries, which exhibit high energy density and operating potential, have long cycle lifespan, and have a low self-discharge rate, are commercially available and widely used.

In addition, as recent interest in environmental problems is increasing, research into electric vehicles (EVs), hybrid electric vehicles (HEVs), and the like that can replace vehicles using fossil fuels, such as gasoline vehicles, diesel vehicles, and the like, which are one of the main causes behind air pollution, is underway. As a power source of EVs, HEVs, and the like, a nickel-metal hydride (Ni-MH) secondary battery is mainly used. However, research into lithium secondary batteries having high energy density, high discharge voltage, and high output stability is actively carried out and some of the lithium secondary batteries are commercially available.

A lithium secondary battery has a structure in which an electrode assembly, which includes: a cathode prepared by coating a cathode active material on a cathode current collector; an anode prepared by coating an anode active material on an anode current collector; and a porous separator disposed between the cathode and the anode, is impregnated with a lithium salt-containing non-aqueous electrolyte.

Such lithium secondary batteries require a certain level or higher of porosity of an electrode in consideration of ionic conductivity of active materials.

However, excess reduction in porosity of an electrode occurs in a process of preparing an electrode slurry including an electrode active material and, consequently, rapid decrease in C-rate may be caused.

Secondary batteries require a certain level or higher of C-rate according to individual applications and, in particular, secondary batteries for power tools which require high power or secondary batteries for EVs and HEVs require much higher C-rate.

Therefore, there is an urgent need to develop a technology that may address the above-described problems.

DISCLOSURE

Technical Problem

Therefore, the present invention has been made to solve the above problems and other technical problems that have yet to be resolved.

As a result of a variety of extensive and intensive studies and experiments, the inventors of the present invention confirmed that, when lithium titanium oxide, a surface of which is coated with a phosphate-based compound as a crosslinked polymer, is used as an anode active material, desired effects may be achieved, thus completing the present invention.

Technical Solution

In accordance with one aspect of the present invention, provided is an anode for secondary batteries in which an anode mixture including an anode active material is coated on a current collector, wherein the anode active material includes lithium titanium oxide (LTO) particles provided on a surface thereof with a cross-linked polymer coating layer, wherein the LTO particles with the cross-linked polymer coating layer formed thereon retain a porous structure formed therebetween, and a cross-linked polymer of the coating layer is a phosphate-based compound.

The anode according to the present invention uses LTO, a surface of which is coated with a phosphate-based compound, as an anode active material and thus may enhance power output characteristics and may also enhance lifespan due to a stabilized electrode interface.

In particular, the LTO particles retain a predetermined porous structure even though the coating layer is formed on the surfaces of the LTO particles, and thus, a specific surface area of a layer of the anode active material may be increased and connectivity among pores may be enhanced and, consequently, an impregnation ratio of an electrolyte may be increased, which results in enhanced charge and discharge characteristics.

That is, the phosphate-based compound has high reactivity with radicals and thus is considered to enhance electrochemical stability of the anode active material through improvement in progress of polymerization.

In particular, an LTO electrode may accelerate electrolyte decomposition reaction ($Ti^{4+} \leftarrow \rightarrow Ti^{3+}$) during charge and discharge and salt anions may accelerate LTO catalytic and electrochemical reactions. In these aspects, it is considered that a phosphate group may reduce liquid electrolyte decomposition by binding to $Ti^{3+}$ with high stability and reduction reactivity through binding with anions and also serve to suppress structural decomposition of the formed film.

In addition, the LTO used as an anode active material acts as a catalyst and thus may accelerate cross-linking polymerization of the phosphate-based compound and, accordingly, the above-described effects may be maximized.

In an embodiment, the phosphate-based compound may be at least one material selected from the group consisting of a phosphate-based acrylate represented by Formula 1 below, a pyrophosphate-based acrylate represented by Formula 2 below, and a phosphate-based urethane acrylate.

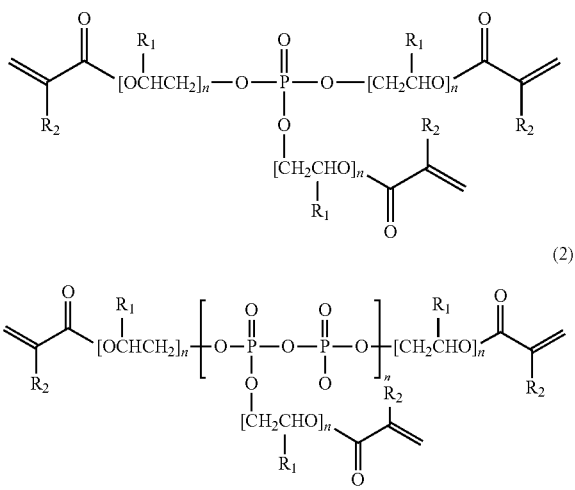

In Formulas 1 and 2, $R_1$ and $R_2$ are each independently hydrogen, a methyl group, or F, and n is an integer of 1 to 20.

Specifically, in Formula 1 and/or Formula 2, $R_1$ may be hydrogen and n may be 1.

The anode may further include a multifunctional compound polymerizable with the phosphate-based compound.

When the coating layer of the anode active material is formed together with the multifunctional compound polymerizable with the phosphate-based compound, various characteristics of a battery may be further enhanced.

That is, when the coating layer of the anode active material is formed by cross-linking polymerization of the phosphate-based compound with high binding affinity through a structure capable of satisfactorily coordinating lithium ions and the multifunctional compound with excellent elasticity, electrochemical properties and mechanical properties of each material may complement each other.

In an embodiment, the multifunctional compound may be at least one material selected from the group consisting of a (meth)acrylic acid ester-based compound, an unsaturated carbonic acid-based compound, a vinyl-based compound.

The (meth)acrylic acid ester-based compound is a (meth)acrylate-based compound having at least two acrylate groups per molecule, and the (meth)acrylate-based compound may be a monomer represented by Formula 3 below or an oligomer thereof.

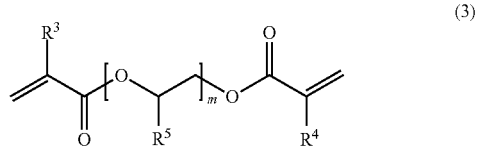

In Formula 3, $R_3$, $R_4$, and $R_5$ are each independently hydrogen or a substituted or unsubstituted $C_1$-$C_4$ alkyl group, and m is an integer of 1 to 20.

In addition, the (metha)acrylic acid ester-based compound may be at least one material selected from the group consisting of diethylene glycol diacrylate (Di(EG)DA), diethylene glycol dimethacrylate (Di(EG)DM), ethylene glycol dimethacrylate (EGDM), dipropylene glycol diacrylate (Di(PG)DA), dipropylene glycol dimethacrylate (Di(PG)DM), ethylene glycol divinyl ether (EGDVE), ethoxylated(6)trimethylolpropane triacrylate (ETMPTA), diethylene glycol divinyl ether (Di(EG)DVE), triethylene glycol dimethacrylate (Tri(EG)DM), dipentaerythritol pentaacrylate (DPentA), trimethylolpropane triacrylate (TMPTA), trimethylolpropane trimethacrylate (TMPTM), propoxylated(3)trimethylolpropane triacrylate (PO(3)TMPTA), propoxylated(6)trimethylolpropane triacrylate (PO(6)TMPTA), poly(ethylene glycol)diacrylate (PA1), and poly(ethylene glycol)dimethacrylate, but embodiments are not limited thereto.

The multifunctional compound may also form various types of copolymers with the phosphate-based compound, e.g., a random copolymer, a block copolymer, a graft copolymer, or the like.

The amount of the phosphate-based compound may be between 0.01 and 50 parts by weight, in particular between 1 and 30 parts by weight, based on 100 parts by weight of the anode active material.

The coating layer of the phosphate-based compound may have a thickness of 0.001 μm to 10 μm, in particular 0.1 μm to 5 μm.

The porosity of the anode may be between 10 and 50%, in particular between 30 and 40%.

The term "porosity" used herein refers to a ratio of a hollow portion of a porous material to a total volume of the porous material and is also referred to as degree of pores or void fraction.

The anode for secondary batteries according to the present invention may be manufactured using a method including: coating an anode slurry including LTO as an anode active material on a current collector and drying the coated current collector (step (A)); forming a phosphate-based compound coating layer on surfaces of LTO particles by impregnating the anode manufactured by step (A) with a solution in which the phosphate-based compound is dissolved (step (B)); and polymerizing the phosphate-based compound through thermal curing, photocuring by irradiation of electron beams or gamma rays, or stabilization reaction at a temperature of 30° C. to 80° C. (step (C)).

In step (B), the amount of the phosphate-based compound may be 0.1 wt % to 30 wt % based on a weight of a solvent.

When the amount of the phosphate-based compound is less than 0.1 wt % based on the weight of the solvent, it is difficult to form the coating layer. On the other hand, when the amount of the phosphate-based compound exceeds 30 wt % based on the weight of the solvent, a transfer rate of lithium ions may decrease and thus battery performance may be deteriorated. This is equally applied to a case in which the multifunctional compound is added to the phosphate-based compound. That is, a total amount (weight) of the phosphate-based compound and the multifunctional compound may be between 0.1 and 30 wt %, in particular between 1 to 20 wt %, based on the weight of the solvent.

The multifunctional compound polymerizable with the phosphate-based compound may be included in the solution of step (B) in an amount of 0.1 wt % to 10 wt %, in particular 0.1 wt % to 0.5 wt %, based on the weight of the solvent. When the amount of the multifunctional compound is too low, effects thereof are insufficient. On the other hand, when the amount of the multifunctional compound is too great, polymerization with the phosphate-based compound may be difficult to implement.

The solution in which the phosphate-based compound is dissolved may include a polymerization initiator, an electrolyte solution (plasticizer), and a lithium salt.

Examples of the polymerization initiator include, without being limited to, azo-based compounds such as 2,2-azobis (2-cyanobutane), 2,2-azobis(methylbutyronitrile), 2,2'-azoisobutyronitrile (AIBN), and azobisdimethyl-valeronitrile(AMVN), peroxy-based compounds such as benzoyl peroxide, acetyl peroxide, dilauryl peroxide, di-tert-butyl peroxide, cumyl hydroperoxide, and hydrogen peroxide, and hydroperoxides. In particular, the polymerization initiator may be AIBN, 2,2'-azobis(2,4-dimethyl valeronitrile) (V65), di-(4-tertbutylcyclohexyl)-peroxydicarbonate (DBC), or the like.

The polymerization initiator decomposes at a temperature of 40° C. to 80° C. to form a radical and may react with monomers by free radical polymerization. In general, free radical polymerization is implemented through initiation reaction whereby highly reactive molecules or active sites are temporarily formed, propagation reaction whereby monomers are added to active chain ends and thus active sites are formed again at the chain ends, chain transfer reaction whereby active sites are transferred to other molecules, and termination reaction whereby an active chain center is destroyed. In addition, polymerization may also be implemented without using a polymerization initiator.

The electrolyte solution also serves as a plasticizer. For example, the electrolyte solution may be an aprotic organic solvent such as N-methyl-2-pyrrolidinone, propylene carbonate (PC), ethylene carbonate (EC), butylene carbonate (BC), dimethyl carbonate (DMC), diethyl carbonate (DEC), ethyl methyl carbonate (EMC), gamma butyrolactone, 1,2-dimethoxy ethane, tetrahydroxy franc, 2-methyl tetrahydrofuran, dimethylsulfoxide, 1,3-dioxolane, formamide, dimethylformamide, dioxolane, acetonitrile, nitromethane, methyl formate, methyl acetate, phosphoric acid triester, trimethoxy methane, dioxolane derivatives, sulfolane, methyl sulfolane, 1,3-dimethyl-2-imidazolidinone, propylene carbonate derivatives, tetrahydrofuran derivatives, ether, methyl propionate, or ethyl propionate. The electrolyte solution may be used alone or in combination of at least two thereof.

The lithium salt is a material that is readily soluble in a non-aqueous electrolyte and thus disintegrates into lithium ions. Examples thereof include LiCl, LiBr, LiI, LiClO$_4$, LiBF$_4$, LiB$_{10}$Cl$_{10}$, LiPF$_6$, LiCF$_3$SO$_3$, LiCF$_3$CO$_2$, LiAsF$_6$, LiSbF$_6$, LiAlCl$_4$, CH$_3$SO$_3$Li, CF$_3$SO$_3$Li, (CF$_3$SO$_2$)$_2$NLi, chloroborane lithium, lower aliphatic carbonic acid lithium, lithium tetraphenyl borate, and imide. These lithium salts may be used alone or at least two thereof may be used in combination.

The lithium salt may be included in an amount of 0.01 wt % to 30 wt %, in particular 0.1 wt % to 20 wt %, based on total solids.

In addition, in order to improve charge/discharge characteristics and flame retardancy, for example, pyridine, triethylphosphite, triethanolamine, cyclic ether, ethylenediamine, n-glyme, hexaphosphoric triamide, nitrobenzene derivatives, sulfur, quinone imine dyes, N-substituted oxazolidinone, N,N-substituted imidazolidine, ethylene glycol dialkyl ether, ammonium salts, pyrrole, 2-methoxy ethanol, aluminum trichloride, or the like may be added to the electrolyte. In some cases, in order to impart incombustibility, the electrolyte may further include a halogen-containing solvent such as carbon tetrachloride, ethylene trifluoride, or the like. In addition, in order to improve high-temperature storage characteristics, the electrolyte may further include carbon dioxide gas.

In another embodiment, the anode for secondary batteries according to the present invention may be manufactured using a method including coating an anode slurry including LTO as an anode active material and the phosphate-based compound on a current collector and drying the coated current collector (step (a)) and polymerizing the phosphate-based compound by performing thermal curing, photocuring by irradiation of electron beams or gamma rays, or stabilization reaction at a temperature of 30° C. to 80° C. on the anode fabricated in step (a).

The present invention also provides a secondary battery including the anode for secondary batteries. The secondary battery is manufactured so as to have a structure in which an electrolyte is included in an electrode assembly including a cathode, an anode, and a separator disposed between the cathode and the anode.

The cathode may for example be manufactured by coating a mixture of a cathode active material, a conductive material, and a binder on a cathode current collector and drying and pressing the coated cathode current collector. As desired, the mixture may further include a filler.

The cathode current collector is generally fabricated to a thickness of 3 to 500 μm. The cathode current collector is not particularly limited so long as it does not cause chemical changes in the fabricated lithium secondary battery and has high conductivity. For example, the cathode current collector may be made of stainless steel, aluminum, nickel, titanium, sintered carbon, aluminum or stainless steel surface-treated with carbon, nickel, titanium, or silver, or the like. The cathode current collector may have fine irregularities at a surface thereof to increase adhesion between the cathode active material and the cathode current collector. In addition, the cathode current collector may be used in any of various forms including films, sheets, foils, nets, porous structures, foams, and non-woven fabrics.

Examples of the cathode active material include, without being limited to, layered compounds such as lithium cobalt oxide (LiCoO$_2$) and lithium nickel oxide (LiNiO$_2$) or compounds substituted with one or more transition metals; lithium manganese oxides represented by Li$_{1+x}$Mn$_{2-x}$O$_4$ where 0≤x≤0.33, such as LiMnO$_3$, LiMn$_2$O$_3$, and LiMnO$_2$; lithium copper oxide (Li$_2$CuO$_2$); vanadium oxides such as LiV$_3$O$_8$, LiV$_3$O$_4$, V$_2$O$_5$, and Cu$_2$V$_2$O$_7$; Ni-site type lithium nickel oxides having the formula LiNi$_{1-x}$M$_x$O$_2$ where M=Co, Mn, Al, Cu, Fe, Mg, B, or Ga, and 0.01≤x≤0.3; lithium manganese composite oxides having the formula LiMn$_{2-x}$M$_x$O$_2$ where M=Co, Ni, Fe, Cr, Zn, or Ta, and 0.01≤x≤0.1 or the formula Li$_2$Mn$_3$MO$_8$ where M=Fe, Co, Ni, Cu, or Zn; LiMn$_2$O$_4$ where some of the Li atoms are substituted with alkaline earth metal ions; disulfide compounds; and Fe$_2$(MoO$_4$)$_3$.

The conductive material is typically added in an amount of 1 to 50 wt % based on the total weight of the mixture including the cathode active material. There is no particular limit as to the conductive material, so long as it does not cause chemical changes in the fabricated battery and has conductivity. Examples of conductive materials include graphite such as natural or artificial graphite; carbon black such as carbon black, acetylene black, Ketjen black, channel black, furnace black, lamp black, and thermal black; conductive fibers such as carbon fibers and metallic fibers; metallic powders such as carbon fluoride powder, aluminum powder, and nickel powder; conductive whiskers such as zinc oxide and potassium titanate; conductive metal oxides such as titanium oxide; and polyphenylene derivatives.

The binder is a component assisting in binding between an electrode active material and the conductive material and in binding of the electrode active material to an electrode current collector. The binder is typically added in an amount of 1 to 50 wt % based on the total weight of the mixture including the cathode active material. Examples of the binder include polyvinylidene fluoride, polyvinyl alcohols, carboxymethylcellulose (CMC), starch, hydroxypropylcellulose, regenerated cellulose, polyvinyl pyrrolidone, tetrafluoroethylene, polyethylene, polypropylene, ethylene-propylene-diene terpolymer (EPDM), sulfonated EPDM, styrene butadiene rubber, fluorine rubber, and various copolymers.

The filler is optionally used as a component to inhibit cathode expansion. The filler is not particularly limited so long as it is a fibrous material that does not cause chemical changes in the fabricated battery. Examples of the filler include olefin-based polymers such as polyethylene and polypropylene; and fibrous materials such as glass fiber and carbon fiber.

The anode may be manufactured by coating an anode active material on an anode current collector and drying the coated anode current collector. In some cases, the above-described components may be further coated on the anode current collector.

The anode current collector is typically fabricated to a thickness of 3 to 500 μm. The anode current collector is not particularly limited so long as it does not cause chemical changes in the fabricated secondary battery and has conductivity. For example, the anode current collector may be made of copper, stainless steel, aluminum, nickel, titanium, sintered carbon, copper or stainless steel surface-treated with carbon, nickel, titanium, or silver, and aluminum-cadmium alloys. Similar to the cathode current collector, the anode current collector may also have fine irregularities at a surface thereof to enhance adhesion between the anode current collector and the anode active material and be used in various forms including films, sheets, foils, nets, porous structures, foams, and non-woven fabrics.

The anode active material may be LTO as described above.

In particular, the LTO may be $Li_4Ti_5O_{12}$, $LiTi_2O_4$, or a mixture thereof and, more particularly, may be $Li_4Ti_5O_{12}$.

In addition, examples of the anode active material include carbon such as hard carbon and graphite-based carbon; metal composite oxides such as $Li_xFe_2O_3$ where $0 \leq x \leq 1$, $Li_xWO_2$ where $0 \leq x \leq 1$, $Sn_xMe_{1-x}Me'_yO_z$ where Me:Mn, Fe, Pb, or Ge; Me':Al, B, P, Si, Groups I, II and III elements, or halogens; $0 \leq x \leq 1$; $1 \leq y \leq 3$; and $1 \leq z \leq 8$; lithium metals; lithium alloys; silicon-based alloys; tin-based alloys; metal oxides such as SnO, $SnO_2$, PbO, $PbO_2$, $Pb_2O_3$, $Pb_3O_4$, $Sb_2O_3$, $Sb_2O_4$, $Sb_2O_5$, GeO, $GeO_2$, $Bi_2O_3$, $Bi_2O_4$, and $Bi_2O_5$; conductive polymers such as polyacetylene; and Li—Co—Ni-based materials, and these anode active materials may be used in combination.

The secondary battery according to the present invention may be a lithium secondary battery, and examples thereof include, without being limited to, a lithium metal secondary battery, a lithium ion secondary battery, a lithium polymer secondary battery, and a lithium ion polymer secondary battery. The secondary battery may be manufactured in various forms. For example, an electrode assembly may be fabricated in various forms including a jelly-roll type, a stack type, a stack/folding type, and the like, and the secondary battery may have a structure in which an electrode assembly is accommodated in a battery case such as a cylindrical can, a rectangular can, or a laminate sheet including a metal layer and a resin layer. Such configuration is well known in the art and thus a detailed description thereof will be omitted herein.

The secondary battery may be used as a power source for small electronic devices and medium and large-scale devices as described below.

The present invention also provides a battery module including the secondary battery as a unit battery and a battery pack including the battery module.

The battery pack may be used as a power source for medium and large-scale devices which require stability at high temperature, long cycle lifespan, and high rate characteristics.

Examples of medium and large-scale devices include, without being limited to, electric motor-driven power tools; electric vehicles (EVs), hybrid electric vehicles (HEVs), and plug-in hybrid electric vehicles (PHEVs); electric two-wheeled vehicles such as e-bikes and e-scooters; electric golf carts; and systems for storing power.

Effects of Invention

As apparent from the fore-going, an anode for secondary batteries according to the present invention uses, as an anode active material, lithium titanium oxide, a surface of which is coated with a phosphate-based compound, and thus, may exhibit excellent high-temperature storage, high power output characteristics, and excellent lifespan characteristics due to a stabilized electrode interface.

BRIEF DESCRIPTION OF THE DRAWINGS

The above and other objects, features and other advantages of the present invention will be more clearly understood from the following detailed description taken in conjunction with the accompanying drawing, in which:

FIG. 1 is a graph showing cycle characteristics measured in a chamber at 45° C. according to Experimental Example 2.

BEST MODE

Now, the present invention will be described in more detail with reference to the following examples. These examples are provided only for illustration of the present invention and should not be construed as limiting the scope and spirit of the present invention.

Example 1

Anode Fabrication $Li_{1.33}Ti_{1.67}O_4$ as an anode active material, Denka black as a conductive material, and PVdF as a binder were added to NMP and mixed therein in a weight ratio of 95:2.5:2.5 to prepare an anode mixture. Subsequently, the anode mixture was coated to a thickness of 200 μm on a Cu foil having a thickness of 20 μm and rolled and dried, thereby completing fabrication of an anode.

The fabricated anode was impregnated in a coating solution prepared by dissolving phosphate-based acrylate represented by Formula a below as a phosphate-based material in DMC as a solvent in an amount of 10 wt % based on a weight of the solvent for 30 minutes to form a coating layer thereon, and the resulting structure was irradiated with electron beams to obtain an anode provided thereon with the coating layer formed of the phosphate-based compound.

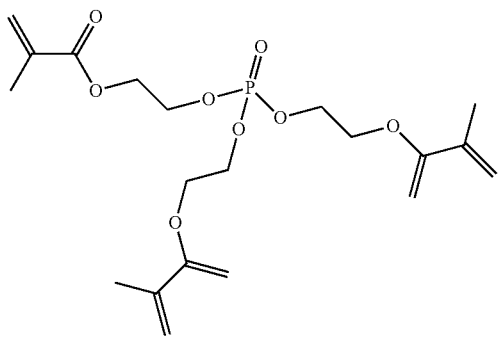

(a)

Manufacture of Battery $LiNi_{0.5}Mn_{1.5}O_4$ as a cathode active material, Denka black as a conductive material, and PVdF as a binder were added to NMP and mixed therein in a weight ratio of 95:2.5:2.5 to prepare a cathode mixture, and the cathode mixture was coated on an Al foil having a thickness of 20 μm and rolled and dried, thereby completing fabrication of a cathode.

Subsequently, a polyethylene film (Celgard®, thickness: 20 μm) as a separator was interposed between the fabricated anode and cathode, and a liquid electrolyte containing 1M $LiPF_6$ dissolved in EC/EMC (=½ (vol %)) was injected thereinto, thereby completing manufacture of a pouch battery.

Example 2

A pouch battery was manufactured in the same manner as in Example 1, except that the pyrophosphate-based acrylate of Formula 2 where $R_1$ is H and n is 1 was used as a phosphate-based material.

Example 3

A pouch battery was manufactured in the same manner as in Example 1, except that dipentaerythritol pentaacrylate (DPentA) as a multifunctional compound was further added to the solution containing the phosphate-based material in an amount of 0.2 wt % based on the weight of the solvent.

Example 4

A pouch battery was manufactured in the same manner as in Example 2, except that DPentA as a multifunctional compound was further added to the solution containing the phosphate-based material in an amount of 0.2 wt % based on the weight of the solvent.

Example 5

Fabrication of Anode $Li_{1.33}Ti_{1.67}O_4$ as an anode active material, Denka black as a conductive material, and PVdF as a binder were added to NMP and mixed therein in a weight ratio of 95:2.5:2.5 to prepare an anode mixture. Subsequently, the anode mixture was coated to a thickness of 200 μm on a Cu foil having a thickness of 20 μm and rolled and dried, thereby completing fabrication of an anode.

The fabricated anode was impregnated in a coating solution prepared by dissolving phosphate-based acrylate represented by Formula a below as a phosphate-based material in DMC as a solvent in an amount of 0.2 wt % based on a weight of the solvent for 30 minutes to form a coating layer thereon, and the resulting structure was irradiated with electron beams to obtain an anode provided thereon with the coating layer formed of the phosphate-based compound.

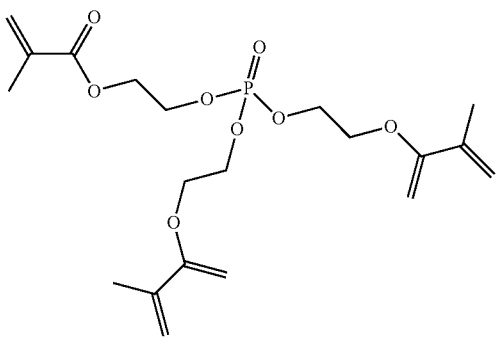

(a)

Manufacture of Battery $LiNi_{0.5}Mn_{1.5}O_4$ as a cathode active material, Denka black as a conductive material, and PVdF as a binder were added to NMP and mixed therein in a weight ratio of 95:2.5:2.5 to prepare a cathode mixture, and the cathode mixture was coated on an Al foil having a thickness of 20 μm and rolled and dried, thereby completing fabrication of a cathode.

Subsequently, a polyethylene film (Celgard®, thickness: 20 μm) as a separator was interposed between the fabricated anode and cathode, and a liquid electrolyte containing 1M $LiPF_6$ dissolved in EC/EMC (=½ (vol %)) was injected thereinto, thereby completing manufacture of a pouch battery.

Example 6

A pouch battery was manufactured in the same manner as in Example 5, except that DPentA as a multifunctional compound was further added to the solution containing the phosphate-based material in an amount of 0.2 wt % based on the weight of the solvent.

Comparative Example 1

A pouch battery was manufactured in the same manner as in Example 1, except that the phosphate-based acrylate was not added to the fabricated anode.

Comparative Example 2

A 2016 coin cell was manufactured in the same manner as in Example 1, except that a coating solution, prepared by adding the compound of Formula a to the solvent in an amount of 40 wt % based on the weight of the solvent, was used.

Experimental Example 1

The batteries (design capacity: 10.2 mAh) manufactured according to Examples 1 to 6 and Comparative Examples 1 and 2 were subjected to formation at 2.75 V, and C-rate charge/discharge cycles of each battery were performed at a voltage of 2.75 V-1.6 V and discharge capacity thereof was confirmed. Results are shown in Table 1 below.

TABLE 1

| | Discharge capacity (1 C) |
|---|---|
| Example 1 | 8.7 mAh |
| Example 2 | 8.2 mAh |
| Example 3 | 8.6 mAh |
| Example 4 | 8.4 mAh |
| Example 5 | 9.3 mAh |
| Example 6 | 8.7 mAh |
| Comparative Example 1 | 9.2 mAh |
| Comparative Example 2 | 7.2 mAh |

Experimental Example 2

5 C/5 C cycle characteristics of the batteries of Examples 1 and 3 and Comparative Examples 1 and 2 were measured during charging and discharging in a chamber at a 45° C. at a voltage of 1.6 V to 2.75 V and 5 C. Measurement results are shown in FIG. 1.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. An anode for secondary batteries, comprising an anode mixture comprising an anode active material, coated on a current collector, wherein the anode active material comprises lithium titanium oxide (LTO) particles, surfaces of which are coated with a cross-linked polymer coating layer, wherein the LTO particles with the cross-linked polymer coating layer formed thereon retain a porous structure formed therebetween, and the cross-linked polymer of the coating layer is a phosphate-based compound, wherein the anode further comprises a multifunctional compound polymerizable with the phosphate-based compound, and the multifunctional compound is at least one material selected from the group consisting of a (meth)acrylic acid ester-based compound, and an unsaturated carbonic acid-based compound, wherein the phosphate-based compound is at least one material selected from the group consisting of a phosphate-based acrylate represented by Formula 1 below, a pyrophosphate-based acrylate represented by Formula 2 below, and a phosphate-based urethane acrylate:

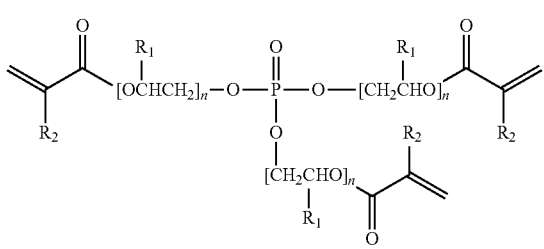
(1)

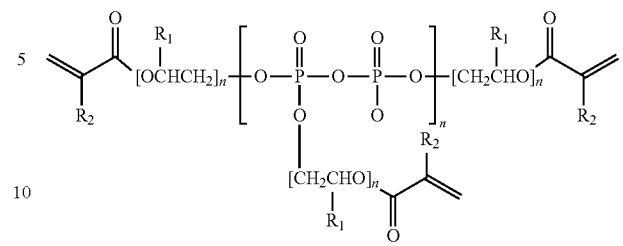
(2)

wherein $R_1$ and $R_2$ are each independently hydrogen, a methyl group, or F, and n is an integer of 1 to 20, and wherein the (meth)acrylic acid ester-based compound is a (meth)acrylate-based compound having at least two acrylate groups per molecule.

2. The anode according to claim 1, wherein the (meth)acrylate-based compound is a monomer represented by Formula 3 below or an oligomer thereof:

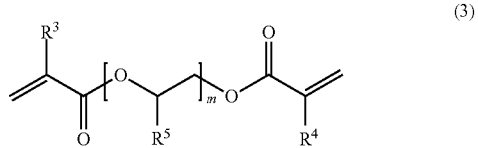
(3)

wherein $R^3$, $R^4$, and $R^5$ are each independently hydrogen or a substituted or unsubstituted $C_1$-$C_4$ alkyl group, and m is an integer of 1 to 20.

3. The anode according to claim 1, wherein the (meth)acrylic acid ester-based compound is at least one material selected from the group consisting of diethylene glycol diacrylate (Di(EG)DA), diethylene glycol dimethacrylate (Di(EG)DM), ethylene glycol dimethacrylate (EGDM), dipropylene diacrylate (Di(PG)DA), dipropylene glycol dimethacrylate (Di(PG)DM), ethylene glycol divinyl ether (EGDVE), ethoxylated(6) trimethylolpropane triacrylate (ETMPTA), diethylene glycol divinyl ether (Di(EG)DVE), triethylene glycol dimethacrylate (Tri(EG)DM), dipentaerythritol pentaacrylate (DPentA), trimethylolpropane triacrylate (TMPTA), trimethylolpropane trimethacrylate (TMPTM), propoxylated(3) trimethylolpropane triacrylate (PO(3)TMPTA), propoxylated(6) trimethylolpropane triacrylate (PO(6)TMPTA), poly(ethylene glycol) diacrylate (PA1), and poly(ethylene glycol) dimethacrylate.

4. The anode according to claim 1, wherein an amount of the phosphate-based compound is 0.01 parts by weight to 50 parts by weight based on 100 parts by weight of the anode active material.

5. The anode according to claim 1, wherein the cross-linked polymer coating layer formed of the phosphate-based compound has a thickness of 0.001 μm to 10 μm.

6. The anode according to claim 1, wherein the anode has a porosity of 10% to 50%.

7. A method of manufacturing the anode for secondary batteries according to claim 1, the method comprising:
coating an anode slurry comprising lithium titanium oxide (LTO) as an anode active material on a current collector and drying the coated current collector;
forming a phosphate-based compound coating layer on surfaces of LTO particles by impregnating the anode manufactured by the above step with a solution in which the phosphate-based compound is dissolved; and polymerizing the phosphate-based compound through thermal curing, photocuring by irradiation of electron beams or gamma rays, or stabilization reaction at a temperature of 30° C. to 80° C.

8. The method according to claim 7, wherein the phosphate-based compound is included in an amount of 0.1 wt % to 30 wt % based on a weight of a solvent.

9. The method according to claim 7, wherein the solution comprises a polymerization initiator, an electrolyte solution (plasticizer), and a lithium salt.

10. The method according to claim 9, wherein the lithium salt is included in an amount of 1 wt % to 30 wt % based on a total weight of solids.

11. The method according to claim 7, wherein a multifunctional compound polymerizable with the phosphate-based compound is included in the solution used in the forming in an amount of 0.1 wt % to 10 wt % based on a weight of a solvent.

12. A method of manufacturing the anode for secondary batteries according to claim 1, the method comprising:

coating an anode slurry comprising lithium titanium oxide (LTO) as an anode active material and the phosphate-based compound on a current collector and drying the coated current collector; and polymerizing the phosphate-based compound by performing thermal curing, photocuring by irradiation of electron beams or gamma rays, or stabilization reaction at a temperature of 30° C. to 80° C. on the anode manufactured by the coating.

13. A secondary battery comprising the anode for secondary batteries according to claim 1.

14. The secondary battery according to claim 13, wherein the secondary battery is a lithium secondary battery.

15. A battery module comprising the secondary battery according to claim 14 as a unit battery.

16. A battery pack comprising the battery module according to claim 15.

17. A device comprising the battery pack according to claim 16.

18. The device according to claim 17, wherein the device is an electric vehicle, a hybrid electric vehicle, a plug-in hybrid electric vehicle, or a system for storing power.

* * * * *